(12) United States Patent
Abbott

(10) Patent No.: US 6,174,927 B1
(45) Date of Patent: Jan. 16, 2001

(54) EXOTHERMIC CATALYTIC CHEMICAL PROCESS

(76) Inventor: Peter Edward James Abbott, Glebe House, Muirfield Road, Eaglescliffe, Cleveland TS16 9EJ (GB)

(*) Notice: Under 35 U.S.C. 154(b), the term of this patent shall be extended for 0 days.

(21) Appl. No.: 09/142,092
(22) PCT Filed: Jan. 22, 1997
(86) PCT No.: PCT/GB97/00167
  § 371 Date: Apr. 6, 1999
  § 102(e) Date: Apr. 6, 1999
(87) PCT Pub. No.: WO97/31707
  PCT Pub. Date: Sep. 4, 1997

(30) Foreign Application Priority Data

Mar. 1, 1996 (GB) .................................. 9604437

(51) Int. Cl.[7] .................................. C07C 27/00
(52) U.S. Cl. .................. 518/713; 518/700; 518/705; 518/712; 518/728
(58) Field of Search ................... 518/713, 700, 518/705, 728, 712

(56) References Cited

U.S. PATENT DOCUMENTS 4,744,966  5/1988  Grotz .
4,778,662 * 10/1988  Pinto .................................. 422/148
5,424,335  6/1995  Abbott .

FOREIGN PATENT DOCUMENTS 0 080 270  6/1983  (EP) .

* cited by examiner

Primary Examiner—Samuel Barts
Assistant Examiner—J. Parsa

(57) ABSTRACT

An exothermic catalytic process, particularly methanol synthesis, wherein reactants are passed through a fixed bed of a catalyst and heat evolved by the reaction is transferred to at least part of the reactants fed to the catalyst bed by heat exchange means to which said part of the reactants are fed, characterized by operation of the process under conditions whereby increasing the temperature at which said reactants are fed to the catalyst bed has the effect of increasing the temperature to which said reactants are heated in said heat exchange means, and vice versa, and controlling said process by monitoring the temperature of said reactants leaving said heat exchange means and/or entering said bed, decreasing the temperature at which the reactants are fed to said heat exchange means in response to any increase in said monitored temperature from a desired level, and increasing the temperature at which the reactants are fed to said heat exchange means in response to any decrease in said monitored temperature from said desired level.

5 Claims, 3 Drawing Sheets

EXOTHERMIC CATALYTIC CHEMICAL PROCESS

This application is a 371 of PCT/GB97/00167 filed on Jan. 22, 1997.

This invention relates to an exothermic catalytic chemical process and in particular to the control of such processes, especially methanol or ammonia synthesis processes, wherein at least part of the heat evolved during the reaction is employed for pre-heating at least part of the reactants to the desired reaction inlet temperature.

Exothermic catalytic chemical processes are often effected by passing a pre-heated reactants stream, usually gaseous, through a fixed bed of a particulate catalyst for the desired reaction. Heat exchange means are often employed to transfer heat evolved during the reaction to at least part of the inlet reactants stream. Thus an adiabatic catalyst bed may be employed with a heat exchanger downstream of the bed to transfer heat from the effluent from the catalyst bed to the reactants stream to be fed to the catalyst bed. Alternatively, the heat exchanger means may be disposed within the catalyst bed so that heat is transferred from the reactants undergoing the reaction to the reactants to be fed to the bed. An example of a suitable reactor for such a process is described in U.S. Pat. No. 4,778,662 where the heat exchanger means comprises a plurality of tubes extending through at least the inlet portion of the catalyst bed. In this type of reaction, herein termed a tube-cooled reactor, the tubes, which are open at their upper ends, extend into, and communicate with a zone above the top of the catalyst bed. The reactants stream is fed to the lower end of the tubes and passes up the tubes into said zone and then passes down through the catalyst bed outside said tubes. As the reactants pass down through the bed, the reaction proceeds and heat evolved by the reaction is transferred through the walls of the tubes to heat the reactants passing up the tubes.

Exothermic reactions, such as ammonia or methanol synthesis reactions, are generally reversible: production of the desired product is favoured, from equilibrium considerations, by employing relatively low temperatures. However the rate of reaction depends on the catalyst activity and temperature: increasing the reaction temperature generally increases the rate of reaction. The catalysts employed for the reaction generally have an optimum usable temperature. If the temperature is too low, the reaction proceeds only relatively slowly, if at all, while if the temperature is too high, not only may the extent of the reaction be limited by virtue of equilibrium considerations, but also the life of the catalyst may be decreased through thermal sintering of the catalyst. Consequently it is generally desirable to operate at temperatures at which the reaction proceeds at an acceptable rate but to limit the maximum temperature to which the catalyst is subject for any prolonged period of time in order to obtain maximum catalyst life and the desired extent of reaction.

Examination of the temperature profile of the reactants as they pass down the bed in reactors of the aforementioned tube-cooled type reveals that the reactants temperature generally passes through a maximum part way down the catalyst bed. We have devised a method of operation of the process whereby the peak temperature is decreased. While the method of the present invention is of particular applicability to processes in which the aforementioned tube-coated type of reactor is employed, it is also applicable to processes using the other reactor designs wherein the heat evolved during the reaction is used to heat at least part of the reactants fed to the reactor, so that the temperature of the reactants entering the bed is at least in part determined by such heat exchange. Examples of such other designs include reactors with one or more adiabatic beds with a feed/effluent heat exchanger and also reactor designs having a feed/effluent heat exchanger together with a "quench" system wherein additional cool reactants, or one of the reactants, are introduced into a bed, or between bed, to effect cooling of the reactants undergoing the reaction.

In a process wherein the heat evolved by the reaction is used to heat at least part of the reactants fed to the catalyst, the temperature of that part of the reactants fed to the bed will depend on the amount of reaction that is taking place and the temperature of the reactants fed to the heat exchanger in which the heat evolved by the reaction is transferred to the reactants.

For simplicity, the invention will be described in relation to processes employing reactors of the aforesaid tube-cooled type, wherein all of the reactants fed to the bed undergo heating by the heat evolved by the reaction. Extension of the invention to processes using an adiabatic bed and a feed/effluent heat exchanger and/or to processes using a quench gas in addition to heating of the reactants by heat evolved by the reaction will be readily apparent to the skilled person.

We have found that for any given temperature $T_0$ at which the reactants are fed to the heat exchanger, there are two possible operating regimes.

In the first regime, hereinafter termed the stable regime, an upward deviation from the temperature $T_1$ to which the reactants are heated in the heat exchanger and at which the reactants enter the catalyst bed has little effect on the amount of reaction occurring in the bed since the regime is "equilibrium limited", i.e. the reaction rate is limited by equilibrium considerations rather than by catalyst activity and temperature. As a result, the temperature of the catalyst bed changes very little: as a consequence the amount of heat transfer decreases, giving a decrease in the temperature $T_1$. As a consequence the amount of heat transfer decreases, giving a decrease in the temperature T, counteracting the aforesaid upward deviation. Conversely with a downward deviation of $T_1$. The regime is thus stable in the sense that for a given temperature $T_0$ at which the reactants are fed to the heat exchanger, the temperature to which the reactants are heated in the heat exchanger and hence at which they enter the bed tends to maintain itself at a constant value. This is the regime normally used for operation: control of the process, to vary the temperature $T_1$ at which the reactants enter the catalyst bed, can thus be achieved by controlling the temperature $T_0$ at which the reactants are fed to the heat exchanger.

In the other regime, herein termed the metastable regime, the reaction rate is not limited by equilibrium considerations, but is determined by the catalyst activity and temperature. As a consequence, an upward deviation of the temperature $T_1$ at which the reactants are fed to the bed effects a significant increase in the amount of reaction occurring in the bed: as a result the bed temperature increases significantly increasing the amount of heat transferred to the reactants undergoing heating. This in turn leads to a further increase in $T_1$. The result is that the process tends to move away from this operating regime towards the aforesaid stable regime, unless checked by decreasing $T_0$. In the converse situation at the metastable regime, a downward deviation of the temperature $T_1$ at which the reactants are fed to the bed, leads to less reaction in the bed as a result of decreased catalytic activity at the lower temperature. Less heat is thus transferred to the reactants undergoing reaction so the temperature $T_1$ of the reactants entering the bed drops further, leading to still further decrease in the reaction rate and hence the amount of reaction occurring. Unless this temperature decrease is checked, by increasing $T_0$, the reaction will die. Thus in the stable regime, increasing $T_0$ has the effect of increasing the value of $T_1$, while in the metastable regime, increasing $T_0$ has the effect of decreasing $T_1$. For a given value of $T_0$, the temperature $T_1$ for the stable regime is greater than the temperature $T_1$ of the metastable regime.

In the present invention we have found that there are significant advantages in operating in the metastable regime.

Accordingly the present invention provides an exothermic catalytic process wherein reactants are passed through a fixed bed of a catalyst for the desired reaction and heat evolved by the reaction is transferred to at least part of the reactants fed to the catalyst bed by heat exchange means to which said part of the reactants are fed, characterized by operation of the process under conditions whereby increasing the temperature at which said reactants are fed to the heat exchange means has the effect of decreasing the temperature to which said reactants are heated in said heat exchange means, and vice versa, and controlling said process by monitoring the temperature of said reactants leaving said heat exchange means and/or entering said bed, decreasing the temperature at which the reactants are fed to said heat exchange means in response to any upward deviation from said monitored temperature, and increasing the temperature at which the reactants are fed to said heat exchange means in response to any downward deviation from said monitored temperature.

The main benefit of the present invention is that resulting from the lower catalyst bed inlet temperature $T_1$ in the metastable regime compared to that of the stable regime for a given temperature $T_0$ of the feed to the heat exchange means. The lower catalyst bed inlet temperature has been found to give a lower peak temperature in the catalyst bed, resulting in less deterioration of the catalyst with time and hence a longer catalyst life.

Control of the process is possible, despite operation in the metastable state, since the catalyst bed represents a considerable heat sink. Thus an increase in $T_0$ to compensate for a downward deviation of $T_1$ from a desired level can be made before a significant decrease in the bed temperature has occurred that would cause the reaction of die. Likewise a decrease in $T_0$ to compensate for an upward deviation of $T_1$ from a desired level can be made before a significant increase in the bed temperature has occurred that would cause the reaction to change to the stable regime. Changes in $T_0$ to compensate for a change in $T_1$ can be made by any suitable heat source. By providing this heat exchanger with a bypass having a valve to control the flow through the bypass, control of $T_0$ can be achieved simply by means of this valve.

It will be appreciated that if it is desired to change the operating conditions, when accepting operating in the metastable regime, for example from operation at a first control set point for $T_1$ to operation at a second control set point for $T_1$ that is lower than the first control set point for $T_1$, the initial action of the control system after setting the new, lower, second control set point for $T_1$ is to reduce $T_0$. As the operation converges to the new, lower, second control set point for $T_1$, the action of the control system is to increase $T_0$ to a value that is higher than the steady state value of $T_0$ corresponding to the steady state operation at the first control set point for $T_1$.

When using a reactor of the tube-cooled type as aforesaid it is important that the monitored temperature $T_1$ is representative of the temperature of the reactants passing through each of the heat exchange tubes. Thus if there are localized temperature differences within the catalyst bed, the reactants emerging from some tubes may be at a different temperature from that of reactants leaving other tubes. This could lead to the reaction in some portions of the bed drying while in others it may move to the stable regime. To overcome this is desirable to provide means to ensure good mixing of the reactants leaving the tubes before the latter enters the catalyst bed. This helps to ensure that the temperature of the reactants entering the bed is uniform: in the absence of good mixing there is a risk that in some cases reactants leaving a particular tube may pass through the bed adjacent that tube and so exacerbate any temperature differentials. In the absence of good mixing, it may not be possible to control the operation in the metastable regime. Mixing means that may be employed include flow directing devices, such as nozzles at the top of each tube to direct the flow of reactants away from the catalyst bed region adjacent that tube (for example as described in U.S. Pat. No. 3,041,150) and/or baffles and/or swirlers to promote good mixing of the reactants leaving the tubes before entering the catalyst bed.

When employing a tube-cooled reactor, it is not essential that the heat exchange tubes extend through the whole depth of the catalyst bed. Thus, as described in U.S. Pat. No. 4,778,662, there may be an uncooled, adiabatic bed, downstream of the tube-cooled portion.

The invention is of particular utility for the synthesis of methanol using copper-containing catalysts. In such a process a gaseous reactants stream comprising hydrogen and carbon oxides is passed over a fixed bed of a catalyst, such as copper/zinc oxide/alumina catalyst, at a pressure in the range 40 to 150 bar abs., at a catalyst outlet temperature in the range 200–300° C. The catalyst inlet temperature $T_1$ is usually in the range 200–250° C. The temperature $T_0$ required to achieve operation in the metastable regime at such a catalyst inlet temperature will depend upon the nature of the heat exchange means transferring the heat evolved by the reaction to the reactants, but will usually be about 60–100° C. below the desired $T_1$.

Start-up of the process directly into the metastable regime may prove to be difficult and so it is preferred to commence operation in the stable regime and then change the conditions to the metastable regime. This may be achieved by reducing the temperature $T_0$ at which the reactants are fed to the heat exchanger effecting heat transfer from the reaction. As a result of decreasing $T_0$, the temperature $T_1$ to which the reactants are pre-heated, and at which they enter the catalyst bed, falls. When $T_1$ has dropped sufficiently, operation in the metastable regime can be achieved by increasing $T_0$ to the desired value.

BRIEF DESCRIPTION OF DRAWINGS

The invention is illustrated by reference to the accompanying drawings in which

In FIG. 1 there is shown diagrammatically an adiabatic reactor 1 containing a fixed bed of catalyst and a feed/effluent heat exchanger 2. The reactants are heated to a temperature $T_0$ in a heat exchanger 3 and fed at $T_0$ to heat exchanger 2 where they are heated to temperature $T_1$ by heat exchange with the product from the reactor 1. The reactants are thus fed to reactor 1 at the temperature $T_1$. As a result of the adiabatic reaction occurring in the reactor 1, the product leaves the reactor 1 at a temperature $T_2$. To control the process, part of the reactants bypass heat exchanger 3 via a bypass 4 fitted with a valve 5 to control the amount of bypass. A controller 6 monitoring the temperature $T_1$ actuates valve 5 to increase the amount of bypass, and hence decrease temperature $T_0$, in response to an increase in the monitored temperature $T_1$ and vice versa.

In FIG. 2 there is shown a graph showing the heat evolved by the reaction occurring in reactor 1 of FIG. 1 plotted against the temperature $T_1$ at which the reactants enter the catalyst bed. This curve has a "S" shape. Thus at low reactants inlet temperatures, there is relatively little reaction and so little heat is evolved. As the inlet temperature $T_1$ increases, the catalyst activity increases and so the reaction proceeds faster, evolving more heat. At high values of $T_1$ the reaction becomes equilibrium limited so that an increase in the inlet temperature reduces the driving force for the reaction so that the reaction rate slows down, decreasing the rate at which heat is evolved as the temperature $T_1$ increases. Also shown in FIG. 2 is the plot of the heat transferred in the heat exchanger for any given temperature $T_0$ at which the reactants are fed to the heat exchanger. This plot is essentially linear. It is seen that the two graphs start from the same point: thus at a low $T_1$ there is no reaction and so the exit temperature $T_2$ is the same as $T_1$ and so no heat is transferred in the heat exchanger 2. At a certain point, corresponding to a reactants bed inlet temperature of $T_a$, the curve of the heat evolved crosses the heat exchange line. This point is the metastable state: thus at this point, the heat evolved by the reaction equals the heat transferred in the heat exchanger. At higher values of the reactants bed inlet temperature $T_1$, the heat evolved by the reaction exceeds the heat transferred in the heat exchanger until the two lines again cross at a bed inlet temperature of $T_b$. The stable regime corresponds to the bed inlet temperature of $T_b$. At bed temperatures above $T_b$, the heat transferred by the heat exchanger exceeds the heat produced by the reaction.

In the metastable regime, the reaction is primarily governed by the catalyst activity. As shown in FIG. 2, an upward deviation of $T_1$ at which the reactants enter the catalyst bed from the value $T_a$ effects a significant increase in the activity of the catalyst and hence a significant increase in the amount of reaction occurring. As a result more heat is transferred in the heat exchanger giving a further increase in the temperature to which the reactants are preheated and hence at which the reactants enter the catalyst bed. The system thus tends towards the stable regime. Conversely, a downward deviation of the temperature $T_1$ at which the reactants enter the catalyst bed from the temperature $T_a$ effects a significant decrease in the activity of the catalyst and hence a significant decrease in the amount of reaction occurring. As a result less heat is transferred to the reactants being preheated giving a further decrease in the temperature to which the reactants are preheated and hence at which the reactants enter the catalyst bed. The reaction thus tends to die.

In contrast, in the stable regime, the reaction is primarily governed by equilibrium considerations. When equilibrium limited, an increase in temperature reduces the equilibrium concentration of the desired product. The system is thus closer to the equilibrium and so there is less driving force for the reaction. The reaction thus slows down, giving a decrease in the amount of heat evolved and hence transferred to the reactants being pre-heated. Hence an upward deviation of the temperature $T_1$ at which the reactants enter the bed from $T_b$ causes the reaction to slow down so that the amount of heat evolved from the reaction is less than the amount of heat transferred by the heat exchanger. As a result the temperature $T_1$ tends to revert to the $T_b$ value. Conversely, a downward deviation of the temperature $T_1$ at which the reactants enter the catalyst bed from the $T_b$ value moves the system further from equilibrium and so effects an increase in the amount of reaction and hence an increase in the amount of heat transferred to the reactants being preheated. This thus tends to return the temperature $T_1$ to the $T_b$ value.

Figure 3:
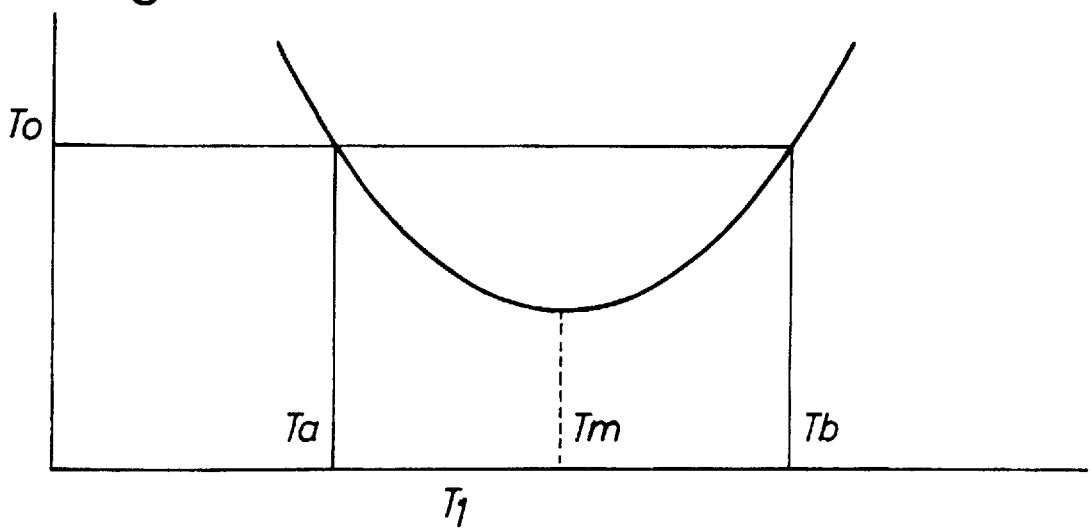
FIG. 3 is a plot of the reactants feed temperature $T_0$ plotted against the temperature $T_1$ at which the reactants enter the catalyst bed.

It is seen that for any given temperature $T_0$ at which the reactants are fed to the heat exchanger, there are in general two $T_1$ temperatures, $T_a$ and $T_b$, at which the system operates, the $T_a$ temperature being the metastable regime and $T_b$ being the stable regime. A diagrammatic representation of the variation of $T_1$ with $T_0$ is shown in FIG. 3.

It is generally difficult to start-up the process with operation in the metastable regime. Therefore it is preferred to start-up the process normally, with operation in the stable regime, i.e. operation at a bed inlet temperature of $T_b$, and then to convert to the metastable regime by reducing the temperature $T_0$ at which the reactants are fed to the heat exchanger effecting heat transfer from the reaction. As a result of decreasing $T_0$, the temperature $T_1$ to which the reactants are pre-heated, and at which they enter the catalyst bed, falls. When $T_1$ has dropped to below the minimum $T_m$ of the curve of $T_0$ plotted against $T_1$ (see FIG. 3), $T_0$ is then increased to the desired value.

Figure 1:
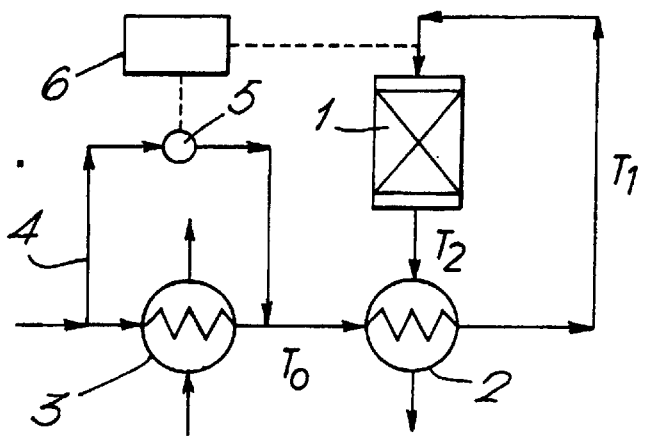
FIG. 1 is a diagrammatic flowsheet showing a reactor and feed/effluent heat exchanger.
Figure 2:
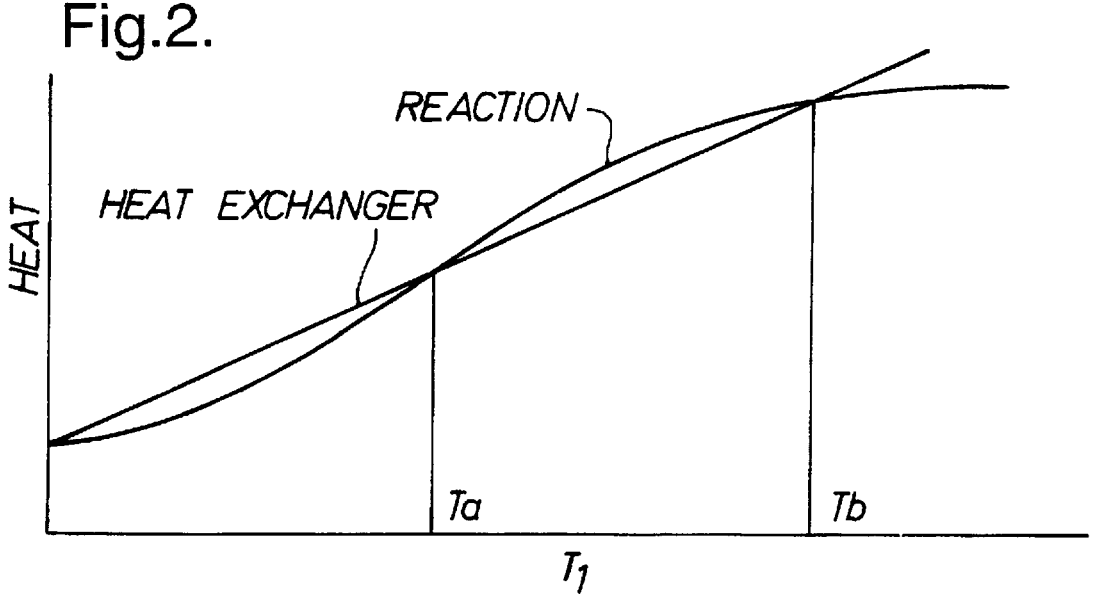
FIG. 2 is a graph showing the heat evolved by the reaction occurring in the reactor of FIG. 1 plotted against the temperature $T_1$ at which the reactants enter the catalyst bed. Also shown in FIG. 2 is the heat transferred in the heat exchanger 1 of FIG.1.
Figure 4:
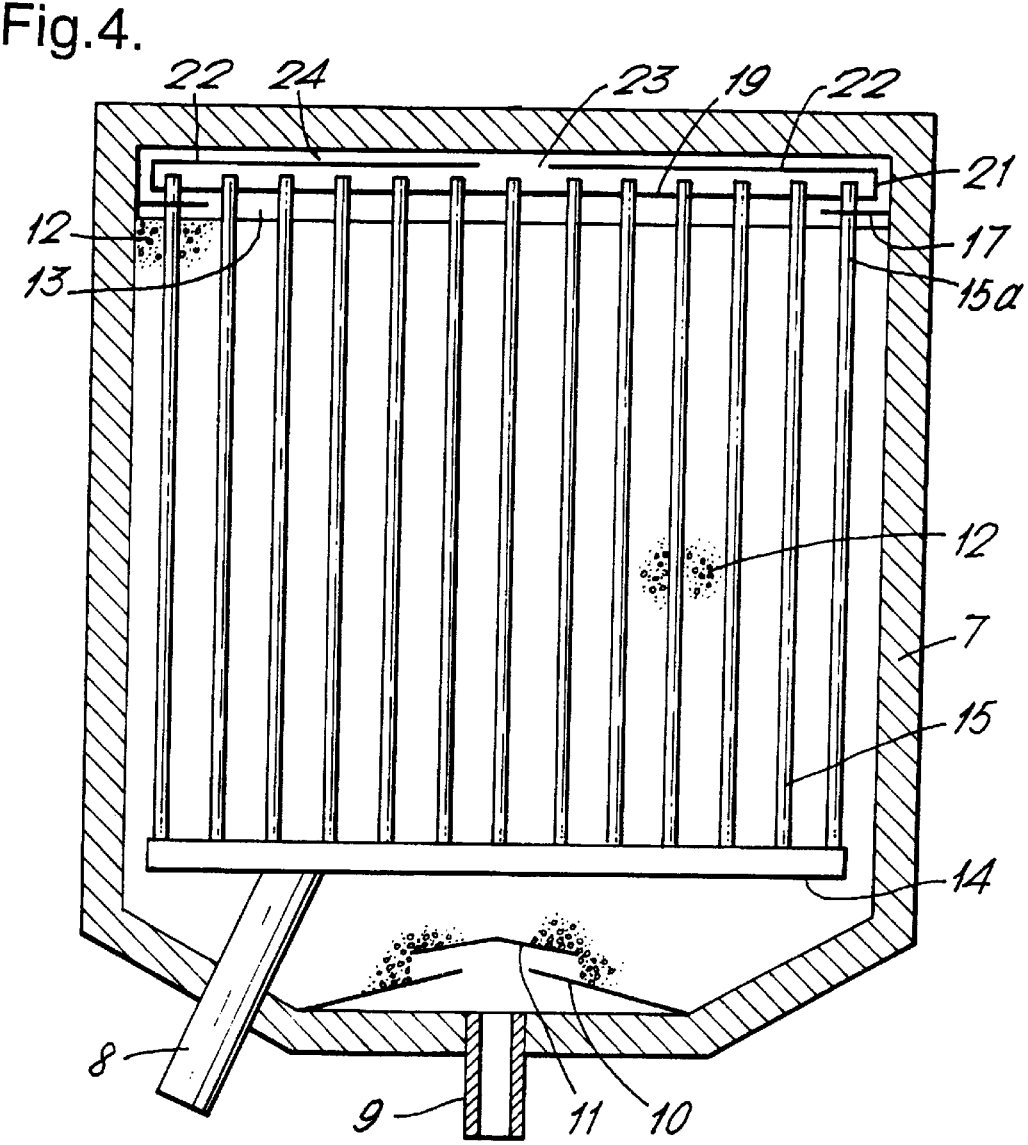
FIG. 4 is a diagrammatic cross section through a tube cooled reactor.
Figure 5:
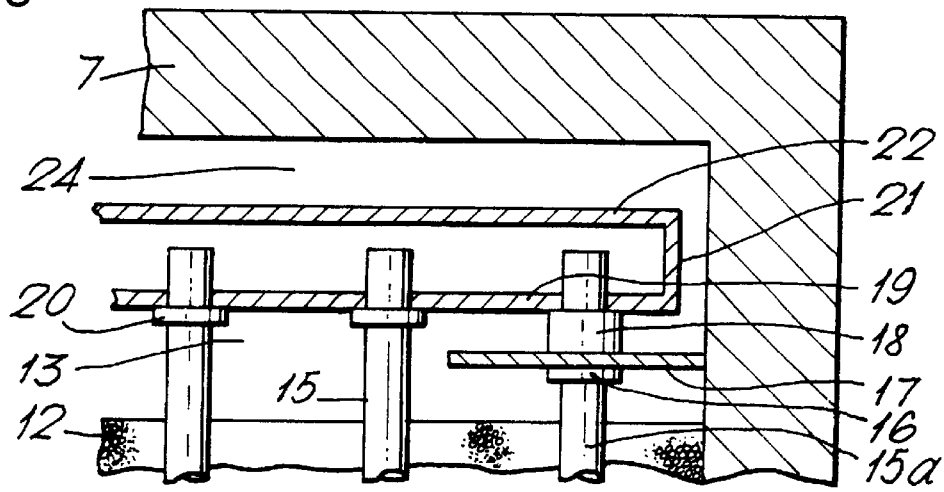
FIG. 5 is an enlarged section of the upper part of the reactor shown in FIG. 4.

FIG. 4 shows a tube-cooled reactor in diagrammatic cross section. FIG. 5 is an enlarged section of the upper part of FIG. 4. The principle of operation is similar to that described above in relation to FIGS. 1 to 3, but in the tube-cooled reaction, the heat exchanger 2 of FIG. 1 is located within the catalyst bed.

The reactor has an outer shell 7 provided with an inlet pipe 8 and an outlet port 9 at its lower end. Located above outlet port 9 is a conical catalyst restraint 10 provided with a conical cover 11 spaced, by means not shown, from restraint 10. The shell is filled, nearly to the top, with a particulate catalyst forming a single catalyst bed 12 with a catalyst-free space 13 above the catalyst bed. Restraint 10 and cover 11 act to provide a catalyst-free space adjacent outlet port 9.

Inlet port 8 is connected, via a header 14, to a plurality of tubes 15 extending up from the header through the catalyst bed 12 into the space 13 above the catalyst bed 12. Tubes 15 are open at their upper ends. Collars 16 are provided adjacent the upper ends of the outermost tubes 15a and these collars 16 support a ring baffle 17 extending round the periphery of the interior of the shell 7. Above baffle 17, the outermost tubes 15a are provided with sleeves 18 which support a plate baffle 19. The remainder of tubes 15 are also provided with collars 20 which also support baffle 19. [For clarity the supporting collars 12 and 16, and sleeves 14, are not shown in FIG. 4, but are shown in FIG. 5]. Baffle 19 has a raised outer wall 21 in turn supporting an inwardly extending ring baffle 22 which has an aperture 23 adjacent its centre to permit gas emerging from the top of tubes 15 to pass into the space 24 between the baffle ring 22 and the upper surface of shell 7. A swirler (not shown) may be provided in aperture 23 to cause additional mixing.

In operation the reactants, at $T_0$, are fed to feed pipe 8. They pass through feed pipe 8 to header 14, and then up through tubes 15. During passage up tubes 15, heat is transferred from the catalyst bed 12 into the reactants passing up tubes 15, thus effecting pre-heating of the reactants. The reactants emerge from the top of the tubes 15 preheated to the desired $T_1$ temperature. The pre-heated reactants then flow from the open upper ends of tubes 15 towards the central axis of the reactor, through aperture 23 in baffle 22 into space 24, down through the annular passage between the wall 21 attached to baffle 19 and the inner wall of the shell 7, and then inwardly through the gap between the underside of baffle 19 and the upper surface of baffle 17 before entering the catalyst bed 12. Baffles 19, 22 and 17 thus serve to promote good mixing of the pre-heated reactants emerging from the upper ends of the tubes 15 before the reactants enter the catalyst bed 12. This ensures in particular that the pre-heated reactants emerging from the upper end of the outermost tubes 15a have an opportunity to mix with the remaining pre-heated reactants before entering the catalyst bed. In the absence of such a mixing device, there is a risk that the pre-heated reactants would enter the catalyst bed near to the tube from which the reactants emerged so that there would be a risk of an uneven temperature distribution. The reactants thus enter and pass down the catalyst bed 12. The desired reaction takes place, liberating heat which is transferred through the walls of tubes 15 to the reactants passing up through those tubes. From the bottom of the bed the reaction product, and any unreacted reactants, pass between cover 11 and catalyst restraint 10 and out of the shell through outlet port 9. As shown in FIG. 4, there may be a portion of the catalyst bed 12 extending below header 14. This provides a final, uncooled, portion of the bed where some further reaction may occur adiabatically.

Figure 6:
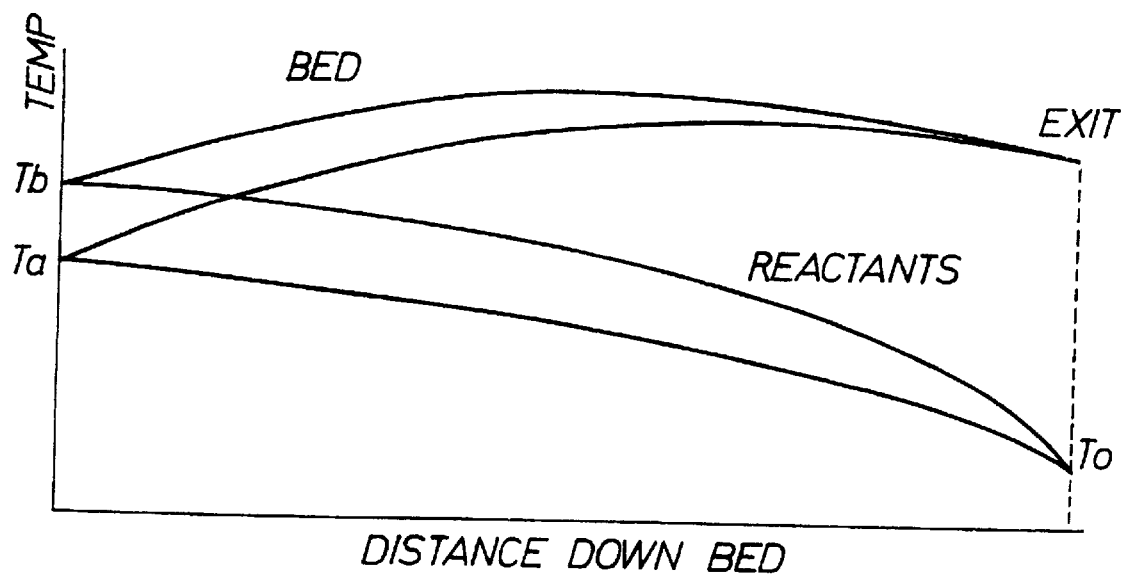
FIG. 6 is a graph showing the temperature profiles in the reactor of FIG. 4 for the stable and metastable states.

In FIG. 6, there is shown typical temperature profiles, for the stable and metastable regimes, for the tubes 15 and the portion of the catalyst bed above header 14 of a reactor of the type shown in FIG. 4. Thus at the lower end, marked by the dotted line, the reactants enter the tubes 15 at $T_0$ and in the metastable regime are heated up to $T_a$ as they pass up through the tubes 15. For the corresponding stable regime the reactants are heated to $T_b$. The reactants then pass down through the catalyst bed. For the stable regime the peak temperature achieved is significantly greater than the peak temperature achieved from the metastable regime. The temperature of the reacted product and any unreacted reactants when they reach the level of the header will generally be a little greater for operation in the stable regime than when operating in the metastable regime.

As indicated above, the process of the invention is controlled by monitoring the temperature $T_1$ of said reactants leaving said heat exchange means and/or entering said bed, decreasing the temperature $T_0$ at which the reactants are fed to said heat exchange means in response to any increase in said monitored temperature, and increasing the temperature $T_0$ in response to any decrease in said monitored temperature.

The temperature $T_1$ may be monitored continuously or intermittently. If the latter, the time period between successive monitorings should be short in relation to the time taken for the system to respond to temperature changes. The monitored temperature $T_1$ may be compared against a preset temperature and the difference signal used to effect the variation in the reactants feed temperature $T_0$. Thus an upward deviation of the monitored temperature $T_1$ from the desired metastable temperature $T_a$ results in the controller decreasing the value of $T_0$ from the value of $T_0$ corresponding to the metastable temperature $T_a$. The magnitude of the decrease in $T_0$ and the duration of the decrease thereof should be such as to return the monitored temperature $T_1$ to the aforesaid metastable temperature $T_a$ before any significant change has occurred in the temperature of the catalyst bed. Known control methods, such as proportional control, may be employed.

The invention is illustrated by the following calculated examples which simulate a synthesis loop wherein a methanol synthesis make-up gas is fed to a loop where it is mixed with recycled unreacted gas. The mixture of make-up gas and recycled unreacted gas is fed to a synthesis reactor of the type shown in FIG. 4 but in which there was no uncooled adiabatic region at the lower end of the reactor. The reactor has a total heat exchange tube surface area of about 206 m$^2$ and contains 13.5 m$^3$ of a copper/zinc oxide/alumina/magnesia composition in the form of cylindrical pellets of length 5.2 mm and diameter 5.4 mm. The effluent from the reactor is then cooled to condense water and methanol which is separated in a separator. Part of the overhead gas from the separator is discharged as a purge while the remainder is recycled as the recycle unreacted gas.

The make-up gas, having the composition shown in the following table A, is fed at a rate of 1000 kmol/hr to the loop. The mixture of make-up gas and recycle gas is fed at a pressure of about 78 bars abs. and at a temperature $T_0$ of 137.4° C. to the lower end of the heat exchange tubes in the synthesis reactor. The calculated flow rates (to the nearest 0.1 kmol/h) of the gas components at various points in the loop are shown in the following table A for operation in both the stable and metastable regimes. In table B there is shown the calculated temperature of the gas both in the tubes and at the corresponding level in the catalyst bed at equal spacings down the tubes.

It is seen from the above tables that the amount of the methanol separated into the crude product is virtually the same in both cases, but whereas the maximum temperature reached in the catalyst bed is about 276° C. for the stable regime, it is only about 261° C. for the metastable regime. Such a decrease in the maximum temperature would significantly prolong the active life of the catalyst.

The heat capacity of the mass of catalysts is sufficient that, provided $T_0$ is adjusted to compensate for any change in $T_1$ within a few minutes, change from operation in the metastable regime to operation in the stable regime, or die-off of the reaction, does not occur. Hence normal temperature controllers with response times of less than one minute are perfectly adequate to maintain control in the metastable regime.

TABLE A

| Gas component | Flow rate of component (kmol/h) | | | | | |
|---|---|---|---|---|---|---|
| | Make-up gas | Recycle gas | Reactor inlet | Reactor outlet | Separated crude product | Purge |
| Stable regime | | | | | | |
| CO | 165.4 | 137.9 | 303.3 | 139.7 | 0.2 | 1.5 |
| CO$_2$ | 119.5 | 329.2 | 448.7 | 338.8 | 6.0 | 3.6 |

TABLE A-continued

| | Flow rate of component (kmol/h) | | | | | |
|---|---|---|---|---|---|---|
| Gas component | Make-up gas | Recycle gas | Reactor inlet | Reactor outlet | Separated crude product | Purge |
| $H_2$ | 693.9 | 3258.9 | 3952.8 | 3295.8 | 0.8 | 36.1 |
| Inerts | 21.3 | 1510.7 | 1532.0 | 1532.0 | 4.6 | 16.7 |
| $H_2O$ | 0.0 | 4.5 | 4.5 | 114.3 | 109.9 | 0.0 |
| $CH_3OH$ | 0.0 | 34.5 | 34.5 | 308.0 | 273.2 | 0.4 |
| total | 1000.0 | 5275.7 | 6275.7 | 5728.6 | 394.6 | 58.4 |
| Metastable regime | | | | | | |
| CO | 165.4 | 142.0 | 307.3 | 143.8 | 0.2 | 1.6 |
| $CO_2$ | 119.5 | 333.1 | 452.6 | 342.9 | 6.0 | 3.7 |
| $H_2$ | 693.9 | 3265.9 | 3959.8 | 3303.4 | 0.8 | 36.7 |
| Inerts | 21.3 | 1495.8 | 1517.1 | 1517.1 | 4.5 | 16.8 |
| $H_2O$ | 0.0 | 4.5 | 4.5 | 114.2 | 109.7 | 0.1 |
| $CH_3OH$ | 0.0 | 34.4 | 34.4 | 307.7 | 272.9 | 0.4 |
| total | 1000.0 | 5275.7 | 6275.7 | 5729.1 | 394.2 | 59.2 |

TABLE B

| | stable regime temperature (° C.) in | | metastable regime temperature (° C.) in | |
|---|---|---|---|---|
| Tube level | tube | bed | tube | bed |
| 1 (top) | 229.3 | 229.3 | 215.3 | 215.3 |
| 2 | 229.0 | 235.0 | 215.1 | 218.7 |
| 3 | 228.0 | 242.6 | 214.6 | 222.5 |
| 4 | 226.1 | 252.5 | 213.5 | 226.8 |
| 5 | 222.7 | 264.2 | 211.9 | 231.8 |
| 6 | 218.0 | 273.1 | 209.6 | 237.4 |
| 7 | 212.1 | 275.7 | 206.4 | 243.6 |
| 8 | 205.6 | 274.5 | 202.1 | 250.3 |
| 9 | 198.6 | 272.0 | 196.8 | 256.4 |
| 10 | 191.2 | 268.9 | 190.4 | 260.3 |
| 11 | 183.3 | 265.5 | 183.1 | 261.2 |
| 12 | 175.0 | 261.7 | 175.0 | 259.7 |
| 13 | 166.3 | 257.6 | 166.4 | 256.7 |
| 14 | 157.1 | 253.0 | 157.2 | 252.6 |
| 15 | 147.5 | 247.8 | 147.5 | 247.8 |
| 16 (bottom) | 137.4 | 242.0 | 137.4 | 242.1 |

What is claimed is:

1. An exothermic catalytic process wherein reactants are passed through a fixed bed of a catalyst for the desired reaction and heat evolved by the reaction is transferred to at least part of the reactants fed to the catalyst bed by heat exchange means to which said part of the reactants are fed, characterised by operation of the process under conditions whereby increasing the temperature at which said reactants are fed to the catalyst bed has the effect of increasing the amount of heat transferred to said reactants in said heat exchange means, and vice versa, and controlling said process by monitoring the temperature of said reactants leaving said heat exchange means and/or entering said bed, decreasing the temperature at which the reactants are fed to said heat exchange means in response to any upward deviation of said monitored temperature from a desired temperature to which said reactants are heated in said heat exchange means, and increasing the temperature at which the reactants are fed to said heat exchange means in response to any downward deviation of said monitored temperature from a desired temperature to which said reactants are heated in said heat exchange means.

2. A process according to claim 1 wherein the heat exchanger means comprises a plurality of substantially vertical tubes immersed in the catalyst bed with the upper ends of the tubes extending into, and communicating with, a catalyst-free zone above said bed, and the reactants are fed to the lower end of said tubes.

3. A process according to claim 1 wherein the reactants that have been pre-heated in the heat exchange means are subjected to mixing before entering the catalyst bed.

4. A process according to claim 1 wherein hydrogen is reacted with carbon oxides using a copper-containing catalyst to produce methanol.

5. A process according to claim 1 wherein operation is commenced by establishing operation under conditions whereby an upward deviation of the temperature at which the reactants are fed to the catalyst bed has the effect of decreasing the amount of heat transferred to said reactants in the heat exchange means, and vice versa, and then reducing the temperature at which the reactants are fed to the heat exchange means until the temperature to which the reactants are pre-heated, and at which they enter the catalyst bed, falls to such an extent that an upward deviation of the temperature at which the reactants are fed to the catalyst bed has the effect of increasing the amount of heat transferred to said reactants in said heat exchange means, and at which they enter the catalyst bed, and then increasing the temperature to which the reactants are fed to the heat exchange means.

* * * * *

UNITED STATES PATENT AND TRADEMARK OFFICE
CERTIFICATE OF CORRECTION

PATENT NO.    : 6,174,927 B1
DATED         : January 16, 2001
INVENTOR(S)   : Abbot It is certified that error appears in the above-identified patent and that said Letters Patent is hereby corrected as shown below:

Please add:
-- [73] Assignee:    Imperial Chemical Industries, PLC
                     London, United Kingdom --

Signed and Sealed this

Twenty-eighth Day of August, 2001

Attest:

NICHOLAS P. GODICI
*Attesting Officer*    *Acting Director of the United States Patent and Trademark Office*